US009981981B2

(12) United States Patent
Finley et al.

(10) Patent No.: US 9,981,981 B2
(45) Date of Patent: *May 29, 2018

(54) TRICYCLIC PROTEASOME ACTIVITY ENHANCING COMPOUNDS

(71) Applicant: President and Fellows of Harvard College, Cambridge, MA (US)

(72) Inventors: Daniel J. Finley, Jamaica Plain, MA (US); Randall W. King, Brookline, MA (US); Byung-Hoon Lee, Cambridge, MA (US); Min J. Lee, Jamaica Plain, MA (US); Timothy C. Gahman, Encinitas, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/572,927

(22) Filed: Dec. 17, 2014

(65) Prior Publication Data

US 2016/0039839 A1    Feb. 11, 2016

Related U.S. Application Data

(63) Continuation of application No. 13/811,129, filed as application No. PCT/US2011/044999 on Jul. 22, 2011, now Pat. No. 8,933,087.

(60) Provisional application No. 61/367,173, filed on Jul. 23, 2010.

(51) Int. Cl.
C07D 495/04 (2006.01)
C07D 487/04 (2006.01)

(52) U.S. Cl.
CPC ......... *C07D 495/04* (2013.01); *C07D 487/04* (2013.01)

(58) Field of Classification Search
CPC .................................................. C07D 495/04
See application file for complete search history.

(56) References Cited

U.S. PATENT DOCUMENTS

| 3,577,420 | A | 5/1971 | Hess et al. |
| 4,146,716 | A | 3/1979 | Cox et al. |
| 6,482,948 | B1 | 11/2002 | Yamada et al. |
| 7,030,240 | B2 | 4/2006 | Dhanoa et al. |
| 8,933,087 | B2 | 1/2015 | Finley et al. |
| 2003/0119829 | A1 | 6/2003 | Stolle et al. |
| 2004/0063943 | A1 | 4/2004 | Eggenweiler et al. |
| 2004/0077664 | A1 | 4/2004 | Eggenweiler et al. |
| 2004/0242595 | A1 | 12/2004 | Eggenweiler et al. |
| 2007/0155777 | A1 | 7/2007 | Burkitt et al. |
| 2010/0120805 | A1 | 5/2010 | Hsieh et al. |
| 2010/0227853 | A1 | 9/2010 | Hoffman et al. |
| 2012/0022046 | A1 | 1/2012 | Byrd et al. |
| 2012/0065200 | A1 | 3/2012 | Barbosa et al. |
| 2013/0045992 | A1 | 2/2013 | Finley et al. |

FOREIGN PATENT DOCUMENTS

| DE | 245 666 | 5/1987 |
| JP | H 01-313480 | 12/1989 |
| JP | 2002-105082 | 4/2002 |
| WO | WO-98/29397 | 7/1998 |
| WO | WO-00/66585 A1 | 11/2000 |
| WO | WO-02/088138 | 11/2002 |
| WO | WO 02/088138 A1 * | 11/2002 |
| WO | WO-03/037898 | 5/2003 |
| WO | WO-2004/065391 A1 | 8/2004 |
| WO | WO-2006/034511 A1 | 3/2006 |
| WO | WO-2007/061764 | 5/2007 |
| WO | WO-2009/029473 A1 | 3/2009 |
| WO | WO-2009/033581 A1 | 3/2009 |
| WO | WO-2010/006032 A1 | 1/2010 |
| WO | WO-2012/062044 A1 | 5/2012 |
| WO | WO-2012/097013 A1 | 7/2012 |
| WO | WO-2013/106535 A1 | 7/2013 |

OTHER PUBLICATIONS

University of Florida. Office of Technology Licensing. "Soluble, Toll-Like Receptor Decoys for Treating Neurodegenerative Diseases." © 2014. Available from: < http://technologylicensing.research.ufl.edu/technologies/14631_soluble-toll-like-receptor-decoys-for-treating-neurodegenerative-diseases >.*
Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Golde, T., et al. "Thinking laterally about neurodegenerative proteinopathies." Journal of Clinical Investigation. (May 2013), vol. 123, No. 5, pp. 1847-1855.*
MedicalNewsToday. "All About Diabetes." (c) Dec. 4, 2010. Available from: < http://web.archive.org/web/20101204070433/http://www.medicalnewstoday.com/info/diabetes/>.*
American Chemical Society (ACS). STN Chemical Abstract Service (CAS) Registry RN Database (2013).
Briel et al., "[Thieno[2,3-d]pyrimidines as antagonists of the glutamate receptors]," Die Pharmazie, 63(11):823-826 (2008).
Ettmayer et al., "Lessons learned from Marketed and Investigational Prodrugs," Journal of Medicinal Chemistry, 47(10):2393-2404 (2004).
Golde et al., "Proteinopathy-induced neuronal senescence: a hypothesis for brain failure in Alzheimer's and other neurodegenerative diseases," Alzheimer's Research & Therapy, 1(5):1-12 (2009).
Han, Hyo-Kyung, "Targeted Prodrug Design to Optimize Drug Delivery," AAPS Pharmsci., 2(1), article 6, pp. 1-11 (2000).

(Continued)

*Primary Examiner* — Noble E Jarrell
*Assistant Examiner* — John S Kenyon
(74) *Attorney, Agent, or Firm* — Foley Hoag LLP

(57) ABSTRACT

Proteinopathies result from the proteasome not acting efficiently enough to eliminate harmful proteins and prevent the formation of the pathogenic aggregates. As described herein, inhibition of proteasome-associated deubiquitinase Usp14 results in increased proteasome efficiency. The present invention therefore provides novel compositions and methods for inhibition of Usp14, enhancement of proteasome activity and treatment of proteinopathies.

16 Claims, 15 Drawing Sheets

(56) References Cited

OTHER PUBLICATIONS

Ma et al., "Membrane Transport Structure Function and Biogenesis: High-affinity Activators of Cystic Fibrosis Transmembrane Conductance Regulator (CFTR) Chloride Conductance Identified by High-throughput Screening," J. Biol. Chem., 277(40):37235-37241 (2002).

Medscape: Self Management of Fatal Familial Insomnia. Part I: What is FFi? (2006) Avaliable from < http://www.ncbi.nlm.nih.gov/pmc/articles/PMC1781306/?report=printable >.

Mayo Clinic, "Alzheimer's disease," (2013), Available from: < http://ww.mayoclinic.com/health/alzheimers-disease/DS00161/METHOD=print&DSECTION=all >.

Mayo Clinic, "Creutzfeldt-Jakob disease," (2012) Available from: < http://www.mayoclinic.com/health/creutzfeldt-jakob-disease/DS00531/METHOD=print&DSECTION=all >.

Mayo Clinic, "Frontotemporal dementia," (2011) Available from: < http://www.mayoclinic.com/health/frontotemporal-dementia/DS00874/METHOD=print&DSECTION=all >.

Mayo Clinic, "Parkinson's disease," (2012) Available from: < http://www.mayoclinic.com/health/parkinsons-disease/DS00295/METHOD=print&DSECTION=all >.

Pédeboscq et al., "Synthesis and study of antiproliferative activity of novel thienopyrimidines on glioblastoma cells," Eur. J. Med. Chem., 45(6):2473-2479 (2010).

Testa, Bernard, "Prodrug research: futile or fertile?," Biochemical Pharmacology, 68:2097-2106 (2004).

International Search Report dated Apr. 6, 2012, from PCT/US2011/044999.

Supplemental European Search Report dated Dec. 5, 2013, from EP 11810459.5.

Card, G. L., et al., "A family of phosphodiesterase inhibitors discovered by cocrystallography and scaffold-based drug design," Nature Biotechnology, 23(2): 201-207 (2005).

CAS Registry No. 1055410-87-1, STN Entry Date Sep. 30, 2008; [1]Benzothieno[2,3-d]pyrimidin-4-amine, N-cyclohexyl-5,6,7,8-tetrahydro-N-(1-methylethyl)-.

CAS Registry No. 1276345-40-4, STN Entry Date Apr. 7, 2011; 2-[propyl(5,6,7,8-tetrahydropyrido[4',3':4,5]thieno[2,3-d]pyrimidin-4-yl)amino]-cyclohexanol; CAS Registry No. 1269394-49-1, STN Entry Date Mar. 21, 2011; 5,6,7,8-tetrahydro-N-methyl-N-(1-methyl-3-pyrrolidinyl)-pyrido[4',3':4,5]thieno[2,3-d]pyrimidin-4-amine; CAS Registry No. 382648-55-7, STN Entry Date Jan. 14, 2002; 5,8-dihydro-6,6-dimethyl-6H-pyrano[4',3':4,5]furo[2,3-d]pyrimidin-4-amine.

CAS Registry Nos. 305796-86-5, 305796-87-6, and 305796-88-7.

Christian, F., et al., "p62 (SQSTM1) and cyclic AMP phosphodiesterase-4A4 (PDE4A4) locate to a novel, reversible protein aggregate with links to autophagy and proteasome degradation pathways," Cellular Signalling, 22:1576-1596 (2010).

Hu, et al., "Structure and mechanisms of the proteasome-associated deubiquitinating enzyme USP14," The EMBO Journal, 24: 3747-3756 (2005).

Lee, B.-H., et al., "Enhancement of Proteasome Activity by a Small-Molecule Inhibitor of Usp14," Nature, 467(7312):179-184 (2010).

Modica, M., et al., "Synthesis and binding properties of novel selective 5-HT$_3$ receptor ligands", Bioroganic & Medicinal Chemistry,12:3891-3901 (2004).

Rosowsky, A., et al., "2,4-Diaminothieno[2,3-d]pyrimidines as Antifolates and Antimalarials. 1. Synthesis of 2,4-Diamino-5,6,7,8-tetrahydrothianaphtheno[2,3-d]pyrimidines and Related Compounds", J. Med. Chem., 16(3):185-188 (1973).

Sleebs, B. E., et al., "Identification of 5,6-substituted 4 aminothieno[2,3-d]pyrimidines as LIMK1inhibitors", Bioroganic & Medicinal Chemistry Letters, 21:5992-5994 (2011).

Bhaskar et al., "Synthesis and Antibacterial Evaluation of Some 4-Substituted 5,6,7.8-Tetrahydro[1]Benzothieno [2,3-d] Pyrimidine Derivatives," Indian Journal of Heterocyclic Chemistry, 16:309-310 (2007).

Bohm et al., "Mitteilung: Basisch substitulerte Thieno[2,3-d]pyrimidine," Pharmazie, 41(1):23-25 (1986).

Konno et al., "Synthesis of Thieno[2,3-d]pyrimidine Derivatives and Their Antifungal Activities," Yakugaku Zasshi (Journal of the Pharmaceutical Society of Japan), 109(7):464-473 (1989).

Ming et al., "Heterocondensed Pyridines by Cycloaddition-Extrusion Sequence of Bi—and Tricyclic 1,3-Oxzainones with N,N-Diethyl-1-propynylamine," Chemische Berichte, 120(8):1427-1431 (1987).

* cited by examiner

| Name | Compound | Percent inhibition* | |
|---|---|---|---|
| | | Usp14/26S | IsoT |
| IU2-1 | | 24 | 0 |
| IU2-2 | | 27 | 0 |
| IU2-3 | | 51 | 0 |
| IU2-4 | | 7 | 0 |
| IU2-5 | | 0 | 0 |
| IU2-6 | | 74 | 0 |

| Name | Compound | Percent inhibition* | |
|---|---|---|---|
| | | Usp14/26S | IsoT |
| IU2-7 |  | 11 | 0 |
| IU2-8 |  | 42 | 0 |
| IU2-9 |  | 0 | 0 |
| IU2-10 |  | 13 | 0 |
| IU2-11 |  | 1 | 0 |

| Name | Compound | Percent inhibition* | |
|---|---|---|---|
| | | Usp14/26S | IsoT |
| IU2-12 |  | 2 | 0 |
| IU2-13 |  | 2 | 0 |
| IU2-14 |  | 23 | 0 |
| IU2-15 |  | 4 | 0 |
| IU2-16 |  | 11 | 0 |

IU2-6

TRICYCLIC PROTEASOME ACTIVITY ENHANCING COMPOUNDS

RELATED APPLICATIONS

This application is a continuation of U.S. patent application Ser. No. 13/811,129, which is the National Stage application of PCT/US2011/044999, filed Jul. 22, 2011, which claims the benefit of priority to U.S. Provisional Patent Application Ser. No. 61/367,173, filed Jul. 23, 2010, the contents of which are hereby incorporated by reference.

GOVERNMENT SUPPORT

This invention was made with U.S. Government support under National Institutes of Health Grant Nos. GM065592, GM66492, and DK082906. The government has certain rights in the invention.

BACKGROUND

The proteasome is a large protein complex that contains 33 distinct subunits. Proteasome complexes function as proteases in part to degrade unneeded or misfolded proteins. Proteasomes regulate many aspects of cell physiology, and proteasome dysfunction has been implicated in a variety of diseases, including cancer and neurodegenerative diseases (Finley D., (2009), Annu Rev. Biochem., 78, 477-513; Hoeller and Dikic, (2009), Nature, 458, 438-444; Demarto and Gillette, (2007), Cell, 129, 659-662); Dahlmann, B. (2007) BCB Biochem 8, Suppl 1, S3; Schartz A L and Ciechanover A (2009) Ann Rev Pharmacol Toxicol 49, 73-96).

Most, but not all, proteasome substrates are targeted for degradation via the covalent attachment of multimeric chains of a small, highly-conserved protein called ubiquitin. Because longer ubiquitin chains interact more strongly with the proteasome than shorter chains (Thrower et al. (2000), EMBO J. 19, 94-102), processes that alter ubiquitin chain length frequently also affect substrate degradation rates. The length of ubiquitin chains attached to substrates tagged for proteasome degradation can be modulated by certain proteasome-associated deubiquitinating enzymes and ubiquitin ligases. These deubiquitinating enzymes and ligases appear to regulate proteasome activity by disassembling or extending proteasome-bound ubiquitin chains.

Mammalian proteasomes contain three major deubiquitinating enzymes: Rpn11, Uch37, and Usp14 (Finley D., (2009), Annu Rev. Biochem., 78, 477-513). Rpn11 removes ubiquitin from the tagged substrate by cutting at the junction between the ubiquitin chain and the substrate. Because the Rpn11-mediated cleavage occurs following a substrate's commitment to proteolysis, but prior to substrate degradation, Rpn11 helps to prevent ubiquitin from being degraded along with the substrate, thus minimizing fluctuations in cellular ubiquitin levels. Additionally, because the proteasome substrate must pass through a narrow translocation channel before encountering the proteasome's sequestered proteolytic sites, removal of a bulky ubiquitin chain may also facilitate substrate translocation. Thus, removal of the ubiquitin chain by Rpn11 promotes substrate degradation through en bloc removal of the ubiquitin chain at a relatively late step in the proteasome pathway (Verma et al., (2002) Science, 298, 611-615; Yao and Cohen, (2002), Nature, 419, 403-407).

In contrast to Rpn11, Uch37 functions prior to the commitment of a substrate to proteasome degradation. Uch37 disassembles ubiquitin chains at the substrate-distal tip (Lam et al., (1997), Nature, 385, 737-740), and its enzymatic activity shortens chains rather than remove them entirely. It has been proposed that chain trimming by Uch37 increases the ability of the proteasome to discriminate between long and short multiubiquitin chains (Lam et al., (1997), Nature, 385, 737-740). Little is known about how Uch37 may regulate proteasome function in cells.

Very little is known about the function of Usp14. However, the yeast ortholog of Usp14, Ubp6, has been suggested to disassemble ubiquitin chains at the substrate-distal tip and to function prior to the commitment of a substrate to proteasome degradation. (Hanna et al., (2006), Cell, 127(7), 1401-1413). Ubp6 is thought to act as a proteasome inhibitor, and prior work on Ubp6 has indicated a noncatalytic mode of proteasome inhibition (Hanna et al., (2006), Cell, 127(7), 1401-1413).

SUMMARY

The present invention provides compositions and methods for the inhibition of Usp14, the enhancement of proteasome activity and the treatment of proteinopathies and other diseases for which enhanced protein breakdown may be therapeutic. Aside from proteinopathies, the enhancement of proteasome activity may be therapeutic for any disease characterized by deficient proteasome activity, or deficient activity of other components of the ubiquitin-proteasome pathway, such as in von Hippel-Lindau disease, spinocerebellar ataxia 1, Angelman syndrome, giant axon neuropathy, inclusion body myopathy with Paget disease of bone and frontotemporal dementia (IBMPFD), and others (Lehman, N. L., (2009), Acta Neuropathologica, 118(3), 329-347; Weihl et al., (2007), Neuromuscular Disorders, 17, 87-87). Enhancing proteasome activity could also be therapeutic for diseases in which proteasome substrates are involved and contribute to pathology, but which do not satisfy a strict definition of proteopathies. For example, numerous oncoproteins are proteasome substrates and their ability to promote cancer could potentially be attenuated by enhancing proteasome activity.

One aspect of the invention relates to a compound represented by formula I,

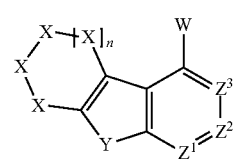

I or a pharmaceutically acceptable salt, solvate, hydrate, prodrug, chemically-protected form, enantiomer or stereoisomer thereof; wherein, independently for each occurrence, W, X, Y, $Z^1$, $Z^2$, $Z^3$ and n are as defined below.

Another aspect of the invention relates to a method of inhibiting the deubiquitination activity of a Usp14 protein comprising contacting the Usp14 protein with a compound of formula I, or pharmaceutically acceptable salt, solvate, hydrate, prodrug, chemically-protected form, enantiomer or stereoisomer thereof.

Another aspect of the invention relates to a method of enhancing protein degradation by a proteasome in a cell comprising contacting the cell with a compound of formula I, or pharmaceutically acceptable salt, solvate, hydrate, prodrug, chemically-protected form, enantiomer or stereoisomer thereof.

Another aspect of the invention relates to a method of treating or preventing a proteinopathy in a subject comprising administering to the subject a compound of formula I, or pharmaceutically acceptable salt, solvate, hydrate, prodrug, chemically-protected form, enantiomer or stereoisomer thereof, or a pharmaceutical composition comprising the same.

Another aspect of the invention relates to a method of enhancing proteasome function in a subject comprising administering to the subject a compound of formula I, or pharmaceutically acceptable salt, solvate, hydrate, prodrug, chemically-protected form, enantiomer or stereoisomer thereof, or a pharmaceutical composition comprising the same.

Another aspect of the invention relates to a method of increasing degradation of Tau, TDP-43 or ataxin-3 in a subject comprising administering to the subject a compound of formula I, or pharmaceutically acceptable salt, solvate, hydrate, prodrug, chemically-protected form, enantiomer or stereoisomer thereof, or a pharmaceutical composition comprising the same.

Additional aspects, embodiments, and advantages of the invention are discussed below in detail. Moreover, the foregoing information and the following detailed description are merely illustrative examples of various aspects and embodiments of the invention, and are intended to provide an overview or framework for understanding the nature and character of the claimed aspects and embodiments.

BRIEF DESCRIPTION OF THE DRAWINGS

FIGS. 9A-9C depict a table of selected compounds of the invention, including percent inhibition values (measured at 8 μM).

DETAILED DESCRIPTION

Figure 1:
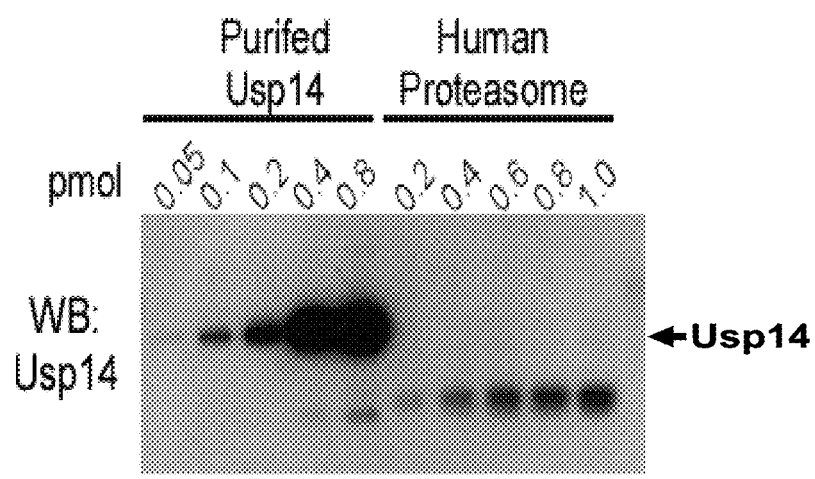
FIG. 1 depicts two panels: panel A shows an immunoblot that was performed using either recombinant Usp14 protein (Purified Usp14) or affinity-purified Usp14 deficient human proteasomes (Human Proteasome) and anti-Usp14 antibody. The band corresponding to Usp14 is indicated; and panel B shows an immunoblot that was performed using anti-Uch37 antibody and Usp14-deficient purified human proteasomes (26S) either untreated (−VS) or treated with Ub-VS (+VS). The band corresponding to Uch37 is indicated. Nonspecific bands are indicated with an asterisk.
Figure 1:
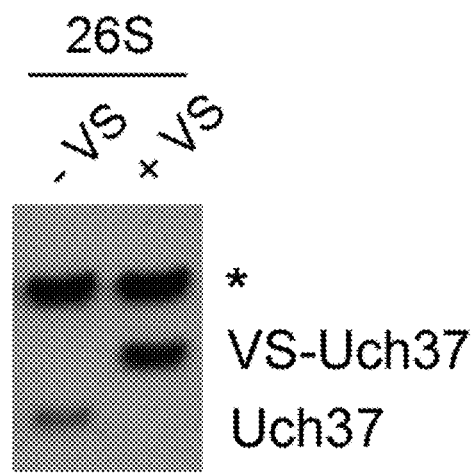

Proteinopathies are a class of diseases and disorders that result from the aggregation of abnormal or misfolded proteins. Often, and perhaps typically, such proteins are eliminated from cells through proteasome-mediated degradation. However, in the case of proteinopathies, the proteasome does not act efficiently enough to eliminate all of the harmful proteins and prevent the formation of the pathogenic aggregates.

As is demonstrated herein, under normal growth conditions, the proteasome is subject to tonic inhibition brought about by the trimming of substrate-bound ubiquitin chains by Usp14. Ubiquitin chain trimming inhibits the proteasome because it removes from proteasome substrates the signal (a ubiquitin chain) that allows recognition by the proteasome; the proteasome-bound substrate can therefore escape without being degraded. Consequently, an inhibitor of chain trimming by Usp14 promotes protein degradation by the proteasome. Thus, as a result of this inhibitory mechanism, the mammalian proteasome pathway does not ordinarily operate at full efficiency because the pathway is partially inhibited by Usp14.

The methods and compositions of the present invention enhance proteasome activity by inhibiting the deubiquitinase activity of Usp14. As demonstrated herein, this enhanced proteasome activity increases the ability of a cell to eliminate abnormal or misfolded proteins, including those associated with human disease. The methods and compositions of the present invention are therefore useful for the enhancement of proteasome function and the treatment of proteinopathies.

Definitions

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure. For example, the $R^5$s in the definition of X may be the same or different; and for each occurrence of X, each of the $R^5$s or $R^3$ (depending on the X) is independently selected for each occurrence.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "cycloalkyl" is a subset of alkyl which refers to cyclic hydrocarbon radical containing from 4 to 15, 4 to 10, or 4 to 7 carbon atoms. Representative examples of cycloalkyl include, but are not limited to, cyclopentyl and cyclobutyl.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinuclidinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6-azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-fluorophenyl) pyridinyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "halo alkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.
The term "nitro" as used herein means a —NO$_2$ group.
The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

As used herein, the term "administering" means providing a pharmaceutical agent or composition to a subject, and includes, but is not limited to, administering by a medical professional and self-administering.

As used herein, the phrases "neurodegenerative disorder" and "neurodegenerative disease" refers to a wide range of diseases and/or disorders of the central and peripheral nervous system, such as neuropathologies, and includes but is not limited to, Parkinson's disease, Alzheimer's disease (AD), amyotrophic lateral sclerosis (ALS), denervation atrophy, otosclerosis, stroke, dementia, multiple sclerosis, Huntington's disease, encephalopathy associated with acquired immunodeficiency disease (AIDS), and other diseases associated with neuronal cell toxicity and cell death.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

As used herein, the phrase "proteinopathy" refers to any disease associated with the accumulation and/or aggregation of abnormal or misfolded proteins. Though proteinopathies are frequently neurodegenerative diseases, proteinopathies also include diseases of other tissues, including the liver, muscle and heart, and include some cancers.

As used herein, the term "subject" means a human or non-human animal selected for treatment or therapy.

As used herein, the phrase "subject suspected of having" means a subject exhibiting one or more clinical indicators of a disease or condition. In certain embodiments, the disease or condition is cancer, a neurodegenerative disorder or pancreatitis.

As used herein, the phrase "subject in need thereof" means a subject identified as in need of a therapy or treatment of the invention.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods of the present invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

Inhibitors of Usp14

One aspect of the invention relates to a compound represented by formula I:

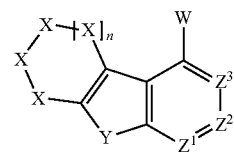

or a pharmaceutically acceptable salt, solvate, hydrate, prodrug, chemically-protected form, enantiomer or stereoisomer thereof; wherein, independently for each occurrence, W is

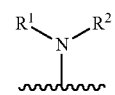

or N-heterocyclyl;

$Z^1$ is

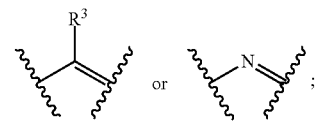

$Z^2$ is

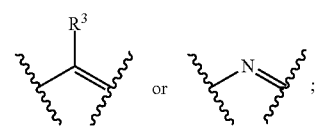

$Z^3$ is

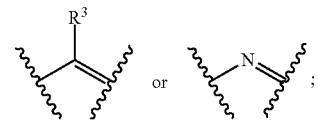

Y is

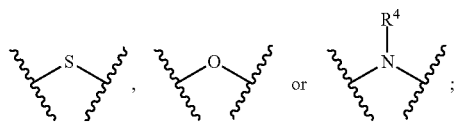

X is

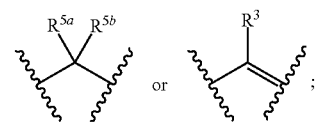

$R^1$ is alkyl, substituted alkyl, haloalkyl, fluoroalkyl, cycloalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl, sufonyl, sulfinyl or —$(CH_2)_m R^6$;

$R^2$ is alkyl, substituted alkyl, haloalkyl, fluoroalkyl, cycloalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl, sulfonyl, sulfinyl or —$(CH_2)_m R^6$;

$R^3$ is hydrogen, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl or silyloxy or —$(CH_2)_m R^7$;

$R^4$ is cycloalkylalkyl, heterocyclylalkyl, aralkyl or heteroalkyl;

$R^{5a}$ is hydrogen, halo, lower alkyl or lower haloalkyl;

$R^{5b}$ is hydrogen, halo, lower alkyl or lower haloalkyl;

$R^6$ is alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl, sulfonyl or sulfinyl;

$R^7$ is alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl or silyloxy;

n is 0, 1 or 2; and m is 1, 2, 3 or 4.

In certain embodiments, the present invention relates to any of the aforementioned compounds, wherein W is

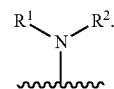

In certain embodiments, the present invention relates to any of the aforementioned compounds, wherein $R^1$ is alkyl, cycloalkyl, heterocyclyl, aryl, heteroaryl, cycloalkylalkyl, heterocyclylalkyl, aralkyl, heteroaralkyl or alkylcarbonyl.

In certain embodiments, the present invention relates to any of the aforementioned compounds, wherein $R^1$ is alkyl.

In certain embodiments, the present invention relates to any of the aforementioned compounds, wherein $R^1$ is lower alkyl.

In certain embodiments, the present invention relates to any of the aforementioned compounds, wherein $R^1$ is methyl, ethyl, isopropyl or isobutyl.

In certain embodiments, the present invention relates to any of the aforementioned compounds, wherein $R^1$ is methyl.

In certain embodiments, the present invention relates to any of the aforementioned compounds, wherein $R^2$ is alkyl, cycloalkyl, heterocyclyl, aryl, heteroaryl, cycloalkylalkyl, heterocyclylalkyl, aralkyl or heteroaralkyl.

In certain embodiments, the present invention relates to any of the aforementioned compounds, wherein $R^2$ is alkyl, cycloalkyl, aryl, aralkyl or alkylcarbonyl.

In certain embodiments, the present invention relates to any of the aforementioned compounds, wherein $R^2$ is lower alkyl, lower cycloalkyl, optionally substituted phenyl, optionally substituted benzyl or lower alkylcarbonyl.

In certain embodiments, the present invention relates to any of the aforementioned compounds, wherein $R^2$ is methyl, ethyl, cyclopropyl, cyclobutyl, cyclopentyl, phenyl, benzyl, or methylcarbonyl.

In certain embodiments, the present invention relates to any of the aforementioned compounds, wherein W is N-heterocyclyl.

In certain embodiments, the present invention relates to any of the aforementioned compounds, wherein W is azetidin1-yl, pyrrolidin-1-yl, piperidin-1-yl, morpholin-1-yl or N-methyl piperazin-1-yl (each optionally substituted with one to five substituents taken from the listed N-heterocyclyl substituents).

In certain embodiments, the present invention relates to any of the aforementioned compounds, wherein $Z^1$ is

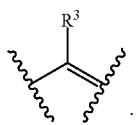

In certain embodiments, the present invention relates to any of the aforementioned compounds, wherein $Z^1$ is

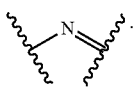

In certain embodiments, the present invention relates to any of the aforementioned compounds, wherein $Z^2$ is

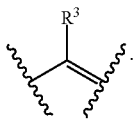

In certain embodiments, the present invention relates to any of the aforementioned compounds, wherein $Z^2$ is

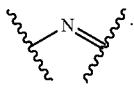

In certain embodiments, the present invention relates to any of the aforementioned compounds, wherein $Z^3$ is

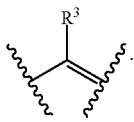

In certain embodiments, the present invention relates to any of the aforementioned compounds, wherein $Z^3$ is

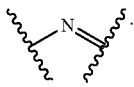

In certain embodiments, the present invention relates to any of the aforementioned compounds, wherein $Z^1$ is

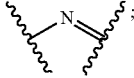 [SMILES: *N=*]

$Z^2$ is

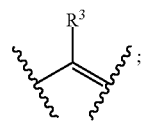

and $Z^3$ is

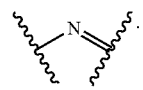

In certain embodiments, the present invention relates to any of the aforementioned compounds, wherein $R^3$ is hydrogen, halo, lower alkyl, lower haloalkyl, cyano, lower alkyloxy, lower haloalkoxy or amino.

In certain embodiments, the present invention relates to any of the aforementioned compounds, wherein $R^3$ is hydrogen.

In certain embodiments, the present invention relates to any of the aforementioned compounds, wherein Y is

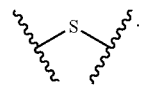

In certain embodiments, the present invention relates to any of the aforementioned compounds, wherein Y is

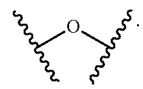

In certain embodiments, the present invention relates to any of the aforementioned compounds, wherein Y is

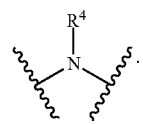

In certain embodiments, the present invention relates to any of the aforementioned compounds, wherein $R^4$ is cycloalkylalkyl.

In certain embodiments, the present invention relates to any of the aforementioned compounds, wherein $R^4$ is heterocyclylalkyl.

In certain embodiments, the present invention relates to any of the aforementioned compounds, wherein $R^4$ is aralkyl.

In certain embodiments, the present invention relates to any of the aforementioned compounds, wherein $R^4$ is heteroaralkyl.

In certain embodiments, the present invention relates to any of the aforementioned compounds, wherein $R^4$ is benzyl substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy or —$(CH_2)_mR^7$.

In certain embodiments, the present invention relates to any of the aforementioned compounds, wherein $R^4$ is p-methoxybenzyl.

In certain embodiments, the present invention relates to any of the aforementioned compounds, wherein X is

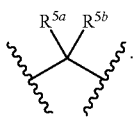

In certain embodiments, the present invention relates to any of the aforementioned compounds, wherein X is

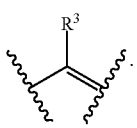

In certain embodiments, the present invention relates to any of the aforementioned compounds, wherein $R^5$ is hydrogen.

In certain embodiments, the present invention relates to any of the aforementioned compounds, wherein n is 0.

In certain embodiments, the present invention relates to any of the aforementioned compounds, wherein n is 1.

In certain embodiments, the present invention relates to any of the aforementioned compounds, wherein n is 2.

In certain embodiments, the present invention relates to any of the aforementioned compounds, wherein m is 1.

In certain embodiments, the present invention relates to any of the aforementioned compounds, wherein m is 2.

In certain embodiments, the present invention relates to any of the aforementioned compounds, wherein m is 3.

In certain embodiments, the present invention relates to any of the aforementioned compounds, wherein m is 4.

In certain embodiments, the present invention relates to any of the aforementioned compounds, wherein the compound is

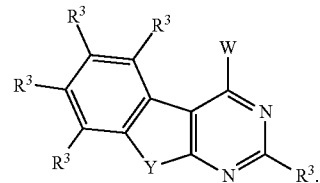

In certain embodiments, the present invention relates to any of the aforementioned compounds, wherein the compound is

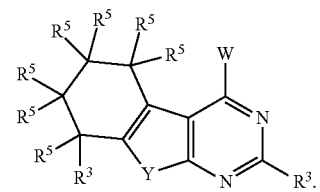

In certain embodiments, the present invention relates to any of the aforementioned compounds, wherein $Z^1$ is

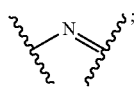

$Z^2$ is

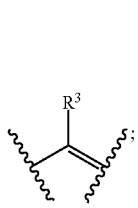

$Z^3$ is

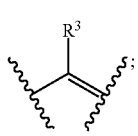

and Y is

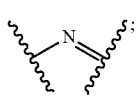

In certain embodiments, the present invention relates to any of the aforementioned compounds, wherein $Z^1$ is

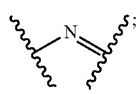

Z² is

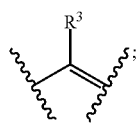

Z³ is

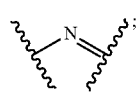

Y is

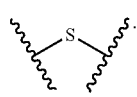

R³ is hydrogen; X is

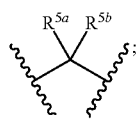

R$^{5a}$ is hydrogen; and R$^{5b}$ is hydrogen.

In certain embodiments, the present invention relates to any of the aforementioned compounds, wherein Z¹ is

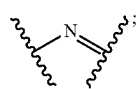 [SMILES: *N=*]

Z² is

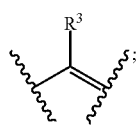

Z³ is

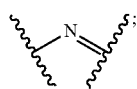

Y is

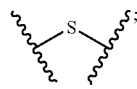

R³ is hydrogen; X is

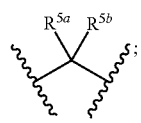

R$^{5a}$ is hydrogen; R$^{5b}$ is hydrogen; and n is 1.

In certain embodiments, the present invention relates to any of the aforementioned compounds, wherein Z¹ is

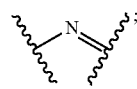

Z² is

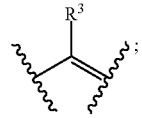

Z³ is

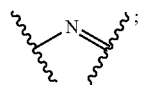

and Y is

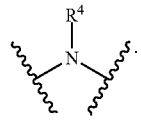

In certain embodiments, the present invention relates to any of the aforementioned compounds, wherein Z¹ is

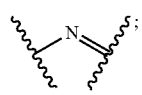

$Z^2$ is

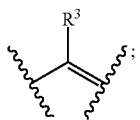

$Z^3$ is

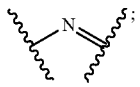 [SMILES: *N=*]

Y is

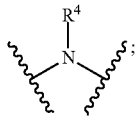

$R^3$ is hydrogen; $R^4$ is aralkyl; X is

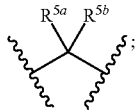

$R^{5a}$ is hydrogen; and $R^{5b}$ is hydrogen.

In certain embodiments, the present invention relates to any of the aforementioned compounds, wherein $Z^1$ is

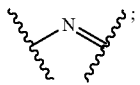

$Z^2$ is

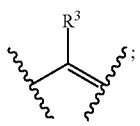

$Z^3$ is

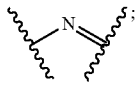

Y is

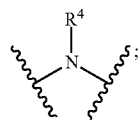

$R^3$ is hydrogen; $R^4$ is p-methoxybenzyl; X is

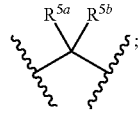

$R^{5a}$ is hydrogen; $R^{5b}$ is hydrogen; and n is 1.

In certain embodiments, the present invention relates to any of the aforementioned compounds, wherein the compound is selected from the group consisting of

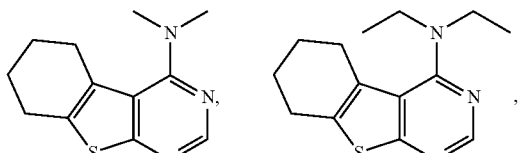

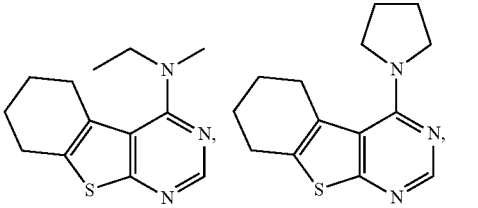

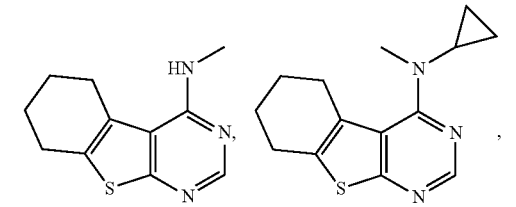

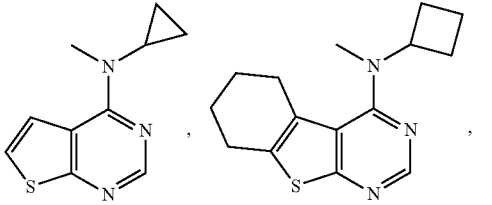

-continued

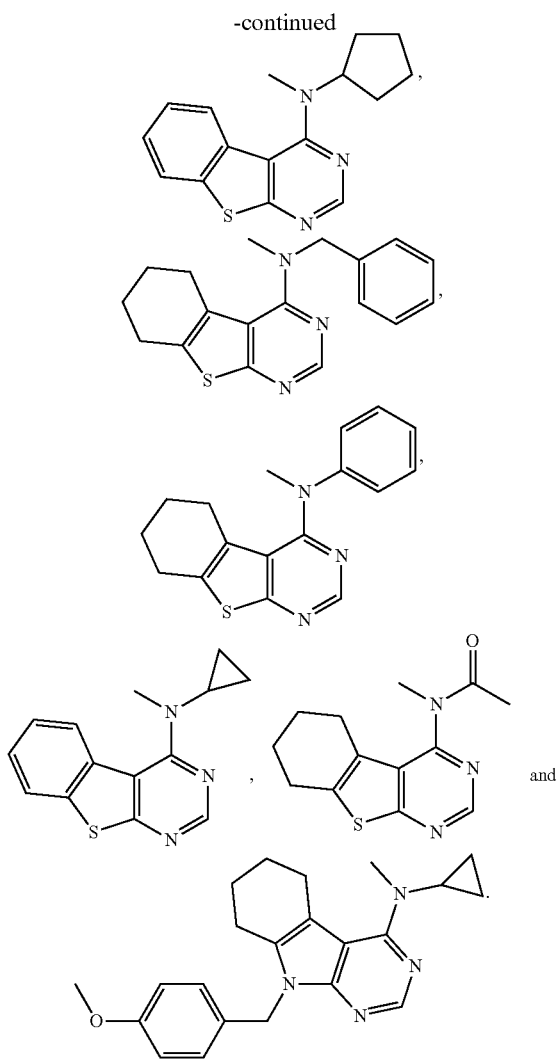

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Pharmaceutically acceptable acid addition salts include those formed with mineral acids such as hydrochloric acid and hydrobromic acid, and those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylamino ethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol or amine of a compound of the invention wherein the free hydrogen of a hydroxyl or amine substituent is replaced by ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O) OCH$_2$C$_6$H$_5$NHCbz); as a t-butoxy amide (—NHC(=O)OC (CH$_3$)$_3$, —NHBoc); a 2-biphenyl-2-propoxy amide (—NHC (=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Pharmaceutical Compositions

The invention provides pharmaceutical compositions comprising inhibitors of Usp14. In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect, the agents of the invention can be administered as such, or administered in mixtures with pharmaceutically acceptable carriers and can also be administered in conjunction with other agents. Conjunctive therapy thus includes sequential, simultaneous and separate, or co-administration of one or more compound of the invention, wherein the therapeutic effects of the first administered has not entirely disappeared when the subsequent compound is administered.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, in certain embodiments, agents of the invention may be compounds containing a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or through a separate reaction of a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may be compounds containing one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds of the invention may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation of the present invention comprises an excipient, including, but not limited to, cyclodextrins, liposomes, micelle forming agents, e.g., bile acids, and polymeric carriers, e.g., polyesters and polyanhydrides; and an agent of the present invention. In certain embodiments, an aforementioned formulation renders orally bioavailable an agent of the present invention.

Methods of preparing these formulations or compositions may include the step of bringing into association an compound of the present invention with the carrier and, optionally, one or more accessory ingredients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Exemplary formulations comprising agents of the invention are determined based on various properties including, but not limited to, chemical stability at body temperature, functional efficiency time of release, toxicity and optimal dose.

The preparations of the present invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Therapeutic Methods of the Invention

The present invention further provides novel therapeutic methods of treating proteinopathies and other diseases for which enhanced protein breakdown may be therapeutic, including neurodegenerative diseases, comprising administering to a subject, (e.g., a subject in need thereof), an effective amount of a compound of the invention.

A subject in need thereof may include, for example, a subject who has been diagnosed with a proteinopathy or a subject who has been treated for a proteinopathy, including subjects that have been refractory to the previous treatment.

The methods of the present invention may be used to treat any proteinopathy. Examples of such proteinopathies include, but are not limited to, Alzheimer's disease, cerebral β-amyloid angiopathy, retinal ganglion cell degeneration, prion diseases (e.g. bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g. frontotemporal dementia, Parkinson's disease, progressive supranuclear palsy, corticobasal degeneration, frontotemporal lobar degeneration), frontotemporal lobar degeneration, amyotrophic lateral sclerosis, Huntington's disease, familial British dementia, Familial Danish dementia, hereditary cerebral hemorrhage with amyloidosis (Icelandic), CADASIL, Alexander disease, Seipinopathies, familial amyloidotic neuropathy, senile systemic amyloidosis, serpinopathies, AL amyloidosis, AA amyloidosis, type II diabetes, aortic medial amyloidosis, ApoAI amyloidosis, ApoII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylois, seminal vesical amyloid, cystric fibrosis, sickle cell disease, critical illness myopathy, von Hippel-Lindau disease, spinocerebellar ataxia 1, Angelman syndrome, giant axon neuropathy, inclusion body myopathy with Paget disease of bone and frontotemporal dementia (IBMPFD).

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use of an agent that modulates a autotrophy-associated gene product and a second agent, e.g. another agent useful for the treatment of the autophagy-related disease, may reduce the required dosage for any individual agent because the onset and duration of effect of the different compounds and/or agents may be complimentary.

One aspect of the invention relates to a method of inhibiting the deubiquitination activity of a Usp14 protein comprising contacting the Usp14 protein with any one of the aforementioned compounds, or a pharmaceutically acceptable salt, solvate, hydrate, prodrug, chemically-protected form, enantiomer or stereoisomer thereof.

Another aspect of the invention relates to a method of enhancing protein degradation by a proteasome in a cell comprising contacting the cell with any one of the aforementioned compounds, or a pharmaceutically acceptable salt, solvate, hydrate, prodrug, chemically-protected form, enantiomer or stereoisomer thereof.

Another aspect of the invention relates to a method of treating or preventing a proteinopathy in a subject comprising administering to the subject any one of the aforementioned compounds, or a pharmaceutically acceptable salt, solvate, hydrate, prodrug, chemically-protected form, enantiomer or stereoisomer thereof.

In certain embodiments, the present invention relates to any of the aforementioned methods, wherein the proteinopathy is selected from the group consisting of Alzheimer's disease, cerebral β-amyloid angiopathy, retinal ganglion cell degeneration, bovine spongiform encephalopathy, kuru, Creutzfeldt-Jakob disease, variant Creutzfeldt-Jakob disease, Gerstmann-Straussler-Scheinker syndrome, fatal familial insomnia, frontotemporal dementia, Parkinson's disease, progressive supranuclear palsy, corticobasal degeneration, frontotemporal lobar degeneration, frontotemporal lobar degeneration, amyotrophic lateral sclerosis, Huntington's disease, familial British dementia, Familial Danish dementia, hereditary cerebral hemorrhage with amyloidosis (Icelandic), CADASIL, Alexander disease, familial amyloidotic neuropathy, senile systemic amyloidosis, serpinopathies, AL amyloidosis, AA amyloidosis, type II diabetes, aortic medial amyloidosis, ApoAI amyloidosis, ApoII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylois, seminal vesical amyloid, cystic fibrosis, sickle cell disease and critical illness myopathy.

In certain embodiments, the present invention relates to any of the aforementioned methods, wherein the proteinopathy is Alzheimer's disease, frontotemporal lobar degeneration, amyotrophic lateral sclerosis or Machado-Joseph disease.

Another aspect of the invention relates to a method of treating or preventing a disease, for which enhanced protein breakdown may be therapeutic, in a subject comprising administering to the subject any one of the aforementioned compounds, or a pharmaceutically acceptable salt, solvate, hydrate, prodrug, chemically-protected form, enantiomer or stereoisomer thereof, or a pharmaceutical composition thereof.

In certain embodiments, the present invention relates to any of the aforementioned methods, wherein the disease is selected from the group consisting of von Hippel-Lindau disease, spinocerebellar ataxia 1, Angelman syndrome, giant axon neuropathy, inclusion body myopathy with Paget disease of bone and frontotemporal dementia (IBMPFD).

Another aspect of the invention relates to a method of enhancing proteasome function in a subject comprising administering to the subject any one of the aforementioned compounds, or a pharmaceutically acceptable salt, solvate, hydrate, prodrug, chemically-protected form, enantiomer or stereoisomer thereof, or a pharmaceutical composition thereof.

Another aspect of the invention relates to a method of increasing degradation of Tau, TDP-43 or ataxin-3 in a subject comprising administering to the subject any one of the aforementioned compounds, or a pharmaceutically acceptable salt, solvate, hydrate, prodrug, chemically-protected form, enantiomer or stereoisomer thereof, or a pharmaceutical composition thereof.

In certain embodiments, the present invention relates to any of the aforementioned methods, wherein said subject is human.

EXAMPLES

The invention now being generally described, will be more readily understood by reference to the following Examples, which are included merely for purposes of illustration of certain aspects and embodiments of the present invention, and are not intended to limit the invention.

Example 1—Synthesis of Inhibitors

One approach to the synthesis of selected compounds of the invention is shown and described below. $^1$H NMR spectra (300 MHz, CDCl$_3$) of IU2-8, IU2-9, IU2-10, IU2-12 and IU2-13 are shown in FIG. 12A-12E.

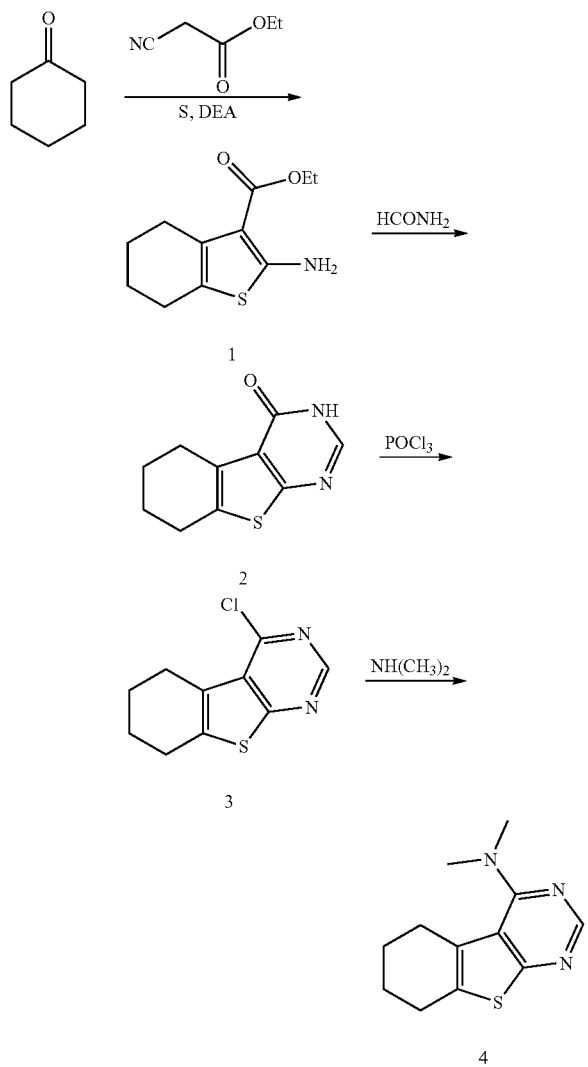

Intermediate 1.

To a suspension of sulfur (11.5 g, 359 mmol) and ethyl 2-cyanoacetate (38.7 g, 342 mmol) in 50 mL of ethanol was added cyclohexan-1-one (33.6 g, 342 mmol) drop-wise at room temperature, followed by addition of diethyl amine (DEA) (25.0 g, 342 mmol), making sure the temperature was maintained below 50° C. The resulting mixture was stirred at 45° C. for 1 h, before being cooled to 0° C. and filtered. The collected material was washed with cold ethanol and dried under vacuum to give Intermediate 1 as yellow solid (57.8 g, yield: 75%).

Intermediate 2.

A suspension of intermediate 1 (7.1 g, 31.5 mmol) in formamide (25 mL) was heated to 145° C. overnight. The resulting mixture was allowed to cool to room temperature and filtered. The collected material was washed with ethyl acetate to provide Intermediate 2 as a light brown solid (5.2 g, yield: 80%).

Intermediate 3.

A solution of intermediate 2 (5.2 g, 25.2 mmol) in phosphorus oxychloride (20 mL) was heated at reflux for 3 h. The solution was concentrated and 100 mL of ice water was added followed by dropwise addition of 10% ammonia hydroxide to pH 8. The resulting mixture was extracted with dichloromethane (3×50 mL) and the combined organics were dried (sodium sulfate), filtered and concentrated. The crude material was purified by flashing chromatography to give Intermediate 3 (4.4 g, yield: 78%).

Compound 4.

A mixture of intermediate 3 (50 mg, 0.22 mmol), dimethylamine (20 mg, 0.44 mmol) and triethyl amine (45 mg, 0.44 mmol) in methanol (10 mL) was stirred at room temperature overnight. The mixture was concentrated and the residue was purified by preparative TLC to provide the final product 4 (45 mg, yield: 88%).

Additional analogs were made by replacing dimethylamine with other suitable amines in the last step of the synthesis.

Example 2—Usp14 Mediates Substrate Deubiquitination

To test whether Usp14 is a potent inhibitor of human proteasomes, a purification procedure was developed to generate proteasomes that lack detectible levels of deubiquitinase Usp14 (modified from Wang et al., (2007), Biochemistry, 46, 3553-3565). Briefly, human proteasomes were affinity-purified on a large scale from a stable HEK293 cell line harboring HTBH-tagged hRpn11. The cells were Dounce-homogenized in lysis buffer (50 mM NaH$_2$PO$_4$ [pH 7.5], 100 mM NaCl, 10% glycerol, 5 mM MgCl$_2$, 0.5% NP-40, 5 mM ATP, and 1 mM DTT) containing protease inhibitors. Lysates were cleared, then incubated with NeutrAvidin agarose resin (Thermo Scientific) overnight at 4° C. The beads were then washed with excess lysis buffer followed by the wash buffer (50 mM Tris-HCl [pH 7.5], 1 mM MgCl$_2$ and 1 mM ATP). For VS-proteasomes, 1 to 1.5 µM of Ub-VS (Boston Biochem) was added to the resin and incubated at 30° C. for 2 h. Residual Ub-VS was removed by washing the beads with at least 20 bed vol of wash buffer. 26S proteasomes were eluted from the beads by cleavage, using TEV protease (Invitrogen).

Using this proteasome purification procedure, human proteasomes were affinity-purified from a hRpn11-tagged line of HEK293 cells. Purification of proteasomes lacking Usp14 but containing related deubiquitinase Uch37 was confirmed by western blot using an anti-Usp14 and anti-Uch37 antibodies (FIGS. 1A and 1B, respectively). The purified Usp14-free proteasome (also described as 26S proteasomes) retained high levels of deubiquitinating activity that could be irreversibly inhibited by treating the proteasome with ubiquitin-vinylsulfone (Ub-VS, Yao et al., (2006) Nat. Cell Biol., 8, 994-1002). Ub-VS inhibits deubiquitination of substrates by forming adducts with the Cys amino acid located in the active site of thiol protease class deubiquitinating enzymes. As demonstrated in FIG. 1B, addition of Ub-VS to 26S proteasomes resulted in enzymatically inactive VS-Uch37 adducts forming with all detectable Uch37.

In order to generate pure, recombinant Usp14 enzyme, GST-Usp14 (WT and C114A variants) was expressed in E.

coli strain Rosetta 2 (DE3) cells (Novagen). Cultures were grown at 37° C. until $OD_{600}$ reached 0.6 to 0.8, and expression was induced overnight with 1 mM IPTG at room temperature. Cells were then harvested in PBS containing protease inhibitors and lysed by French press. The cleared lysates were incubated with GST Sepharose 4B resin (GE Healthcare) at 4° C. for 1 h, and subsequently washed with excess PBS, followed by PBS containing 100 mM NaCl. The GST moiety was removed by thrombin in the cleavage buffer (50 mM Tris-HCl [pH 8.0], 150 mM NaCl, 2.5 mM $CaCl_2$, and 0.1% 2-mercaptoethanol) for 3 h at room temperature. GST-tagged Usp14 proteins for proteasome binding assays were eluted before thrombin cleavage using elution buffer (10 mM reduced glutathione in 50 mM Tris-HCl [pH 8.0]).

Figure 2:
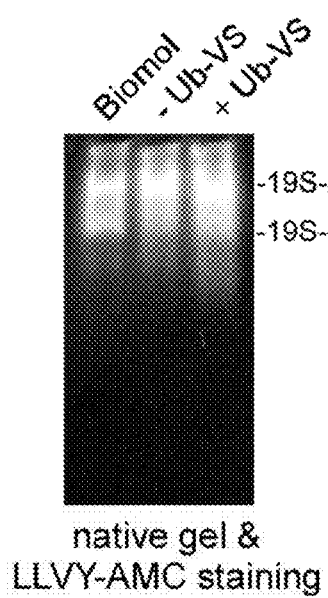
FIG. 2 depicts three panels: panel A shows a nondenaturing gel analysis that had undergone in-gel suc-LLVY-AMC staining (indicating presence of proteasomes) that was performed using commercially available human proteasomes (Biomol), untreated, purified Usp14 deficient human proteasomes (−Ub-VS) or Ub-VS treated purified Usp14 deficient human proteasomes (+Ub-VS); panel B shows a Coomassie Brilliant Blue (CBB) staining of purified, recombinant wild-type Usp14 (Usp14-wt) or catalytically inactive mutant Usp14 (Usp14-C114A) either with or without a GST tag, along with a GST control (GST) and a protein size marker (Marker); and panel C shows the results of a gel-shift assay of proteasomes alone (−), GST and proteasomes (GST), GST tagged wild-type Usp14 and proteasomes (GST-Usp14-wt), GST tagged catalytically inactive mutant Usp14 and proteasomes (GST-Usp14-C114A), untagged wild-type Usp14 and proteasomes (Usp14-wt) or untagged catalytically inactive mutant Usp14 and proteasomes (Usp14-C114A) that had either been stained with in gel suc-LLVY-AMC staining (top, to show the presence of proteasomes) or Coomassie Brilliant Blue (CBB) staining.
Figure 2:
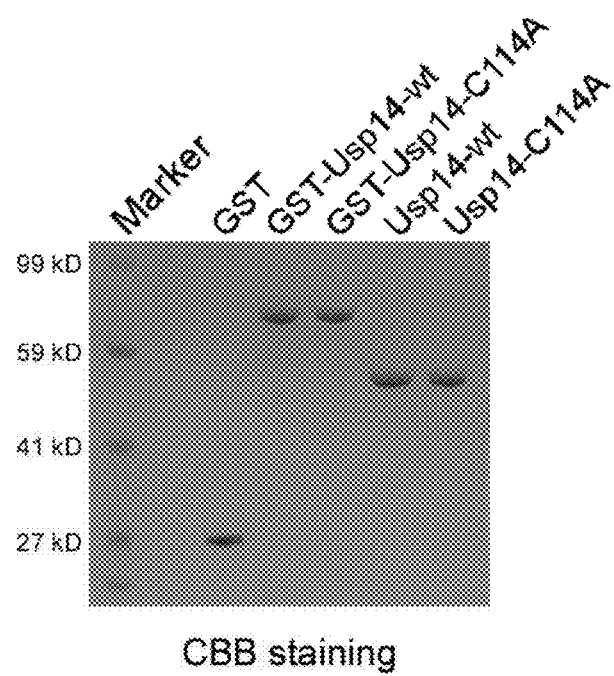
Figure 2:
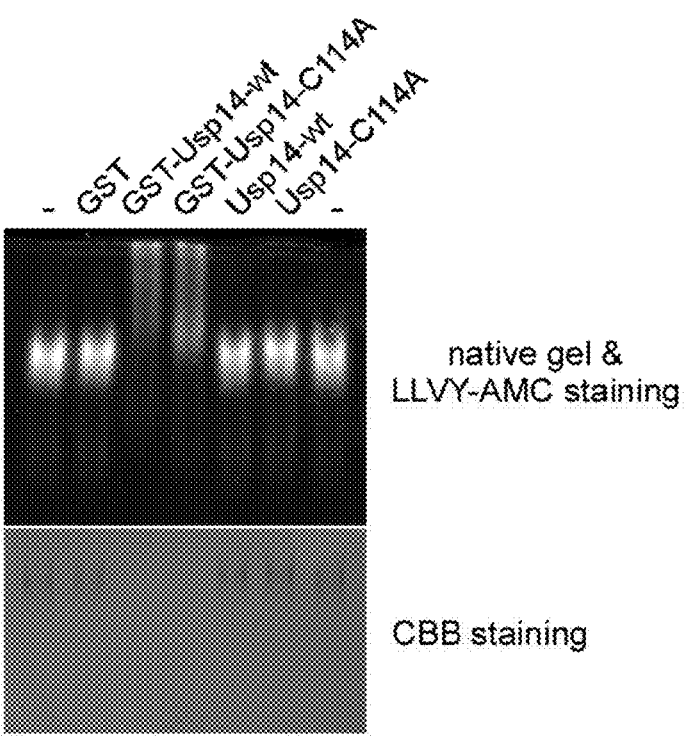
Figure 3:
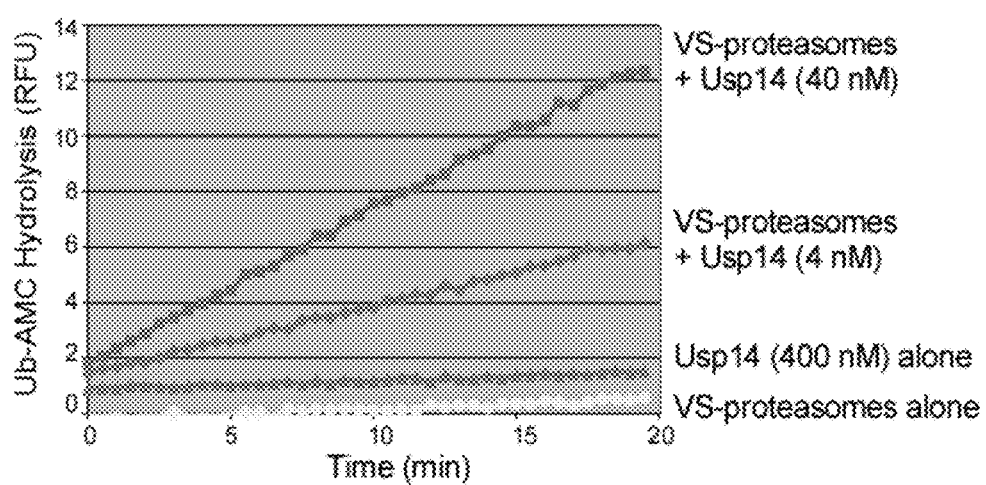
FIG. 3 shows the results of a Ub-AMC hydrolysis assay for Usp14 activity in the presence of Ub-VS treated human proteasomes.

The inhibited "VS-proteasomes" described above, which lack endogenous deubiquitination activity due to Ub-VS treatment, were successfully reconstituted with recombinant Usp14 (FIG. 2). An Ub-AMC hydrolysis assay was performed with 1 nM of Ub-VS treated human proteasome (VS-Proteasome) alone, 400 nM of Usp14 alone, or VS-proteasome that had been reconstituted with 4 or 40 nM of recombinant Usp14 protein. As has been described above, the deubiquitination activity of the VS-proteasome was almost completely inhibited (FIG. 3). In contrast, the reconstituted Usp14/VS proteasome demonstrated substantial deubiquitination activity (FIG. 3). In fact, the Usp14/VS proteasome demonstrated an 800-fold increase in Ub-AMC hydrolyzing activity over that of isolated Usp14 alone (FIG. 3). Thus, the enzymatic activity of Usp14 is increased by its complexing with the proteasome. Therefore, the Ub-AMC assay allows the success of reconstitution to be followed.

Figure 4:
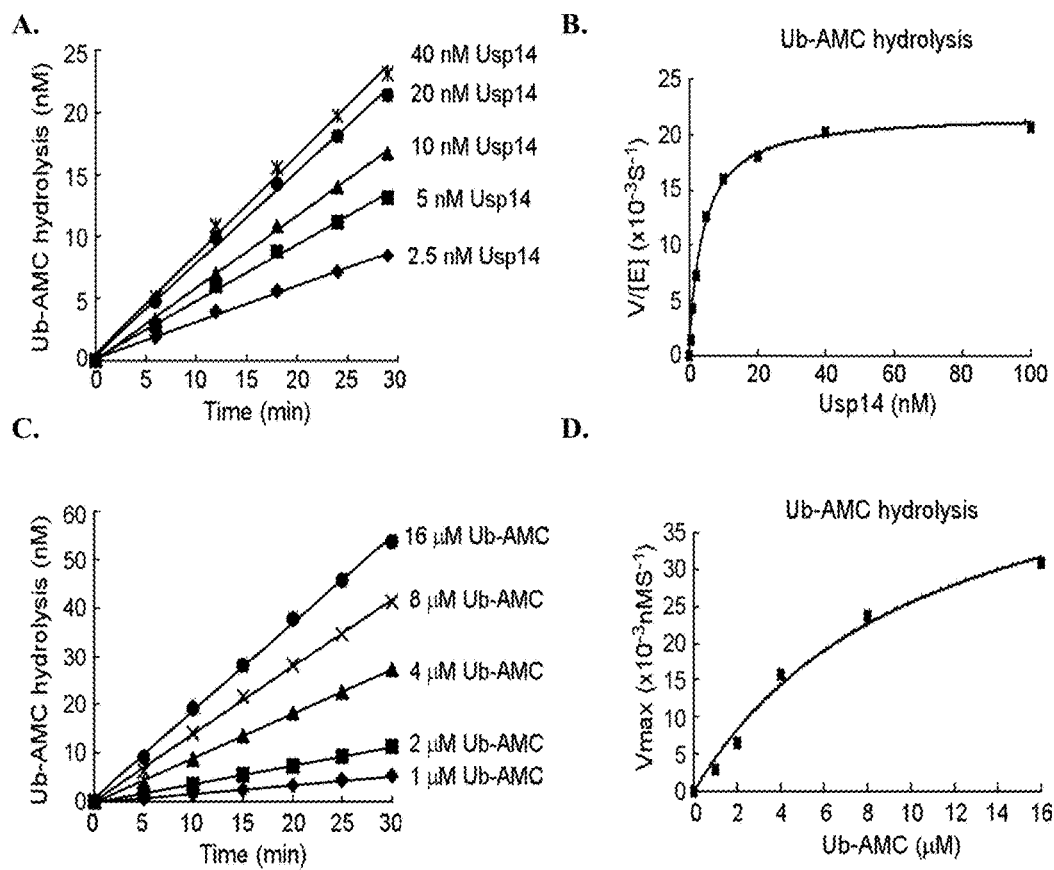
FIG. 4 depicts four panels: panel A shows a plot of the linear kinetics ($R^2>0.99$) of the initial rates of Ub-AMC hydrolysis by Usp14 and proteasome at 1 μM Ub-AMC, 1 nM proteasome, and the indicated concentration of Usp14; panel B shows a Michaelis-Menten plot of Usp14-dependent Ub-AMC hydrolysis in the presence of human proteasome for 25 minutes at 1 μM Ub-AMC, 1 nM proteasome, and the indicated concentration of Usp14; panel C shows a plot of the linear kinetics ($R^2>0.99$) of the initial rates of Ub-AMC hydrolysis by Usp14 and proteasome at 4 nM Usp14, 1 nM proteasome and the indicated concentration of Ub-AMC; and panel D shows a Michaelis-Menten plot of concentration-dependent Ub-AMC hydrolysis in the presence of Usp14 and human proteasome for 30 minutes at 4 nM Usp14, 1 nM proteasome and the indicated concentration of Ub-AMC.

The Ub-AMC assay was also used to examine the kinetics of Ub-AMC hydrolysis by the reconstituted Usp14-proteasome complexes. Ub-AMC hydrolysis by Usp14/VS proteasomes that had been reconstituted with various amounts of Usp14 was monitored over a period of 30 minutes (FIG. 4). Analysis of the results of this assay demonstrated the affinity of Usp14 for the proteasome is approximately 4 nM.

Example 3—Usp14 Inhibits Proteasomal Degradation

Figure 5:
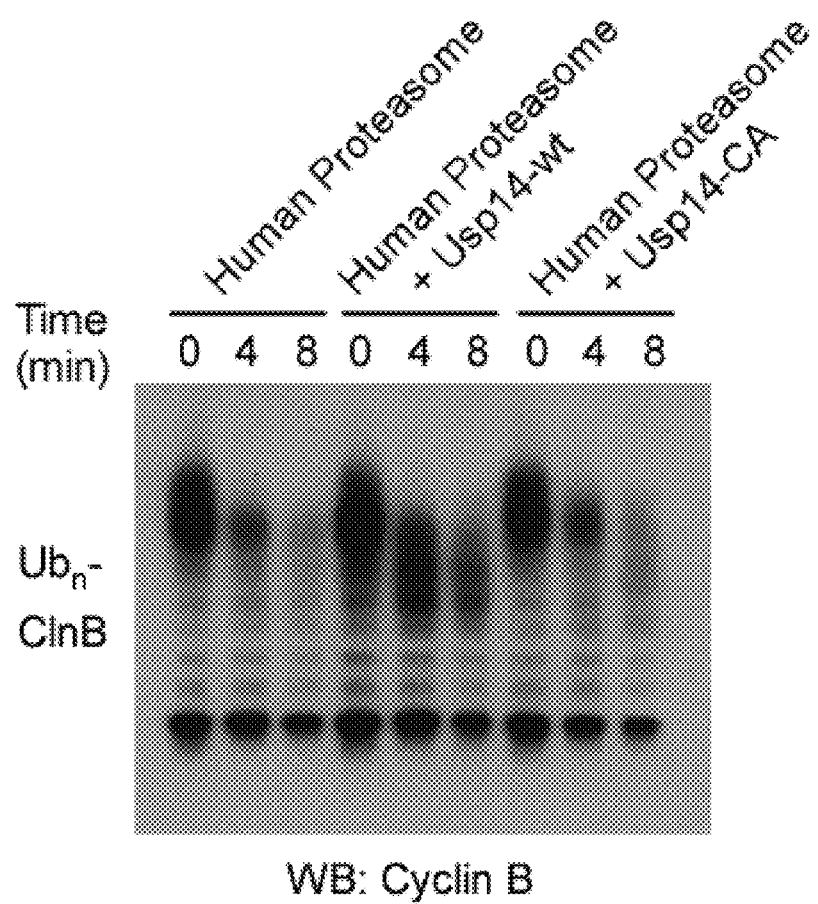
FIG. 5 shows an immunoblot that was performed using an antibody specific for Cyclin B, which also detects polyubiquitinated Cyclin B ($Ub_n$-C1bB). In this experiment, $Ub_n$-C1bB was treated with 26S human proteasome alone, human proteasome and wild-type Usp14 (Usp14-wt) or human proteasome and catalytically inactive Usp14 (Usp14-CA), and subsequently analyzed by immunoblotting.

The effect of Usp14 on the degradation of ubiquitinated substrates was examined using an in vitro degradation assay using the ubiquitin-dependant proteasome substrate polyubiquitinated cyclin B ($Ub_n$-ClnB). In these experiments, $Ub_n$-ClnB was incubated with human proteasomes (4 nM), containing either wild-type or catalytically inactive Usp14 (60 nM). The catalytically inactive Usp used in these assays was Usp14-C114A, which contains a mutation in Usp14's active site for deubiquitination. Notably, both wild-type Usp and Usp14-C114A are able to bind to 26S mammalian proteasomes (FIG. 2). As demonstrated in FIG. 5, Usp14 strongly inhibits the degradation of cyclin B, while the active site mutant of Usp14 showed little inhibitory effect. The lack of inhibition of $Ub_n$-ClnB degradation by the active site mutant indicates that the ubiquitin chain trimming activity of wild-type Usp14 is required for Usp14's inhibition of proteasome degradation. Indeed, extensive trimming of the ubiquitin groups from cyclin B was evident by immunoblot analysis in the samples containing wild-type Usp14, but was nearly eliminated when catalytically inactive Usp14 was used (FIG. 5).

Figure 6:
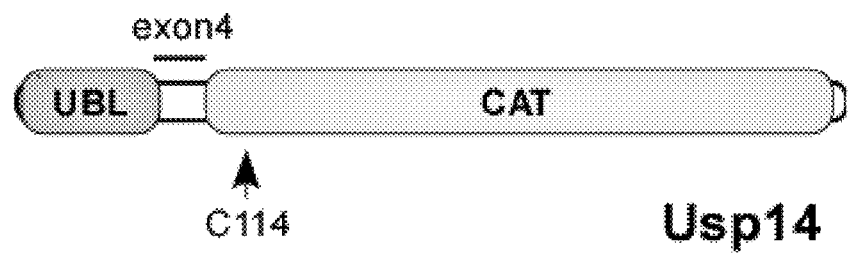
FIG. 6 depicts two panels: panel A shows a diagram of human Usp14, depicting the ubiquitin-like domain (UBL), the catalytic domain (CAT), the location of exon 4 and the position of Cys114; and panel B shows immunoblots that were performed on cellular lysates from human 293 cells that co-expressed Tau along with either wild-type Usp14 (Usp14-wt), catalytically inactive Usp14 (Usp14-CA), short form Usp14 (Usp14-SF) or UBL domain deficient Usp14 (Usp14-ΔUBL) and stained using antibodies specific for Tau, Usp14 or Actin, as indicated.
Figure 6:
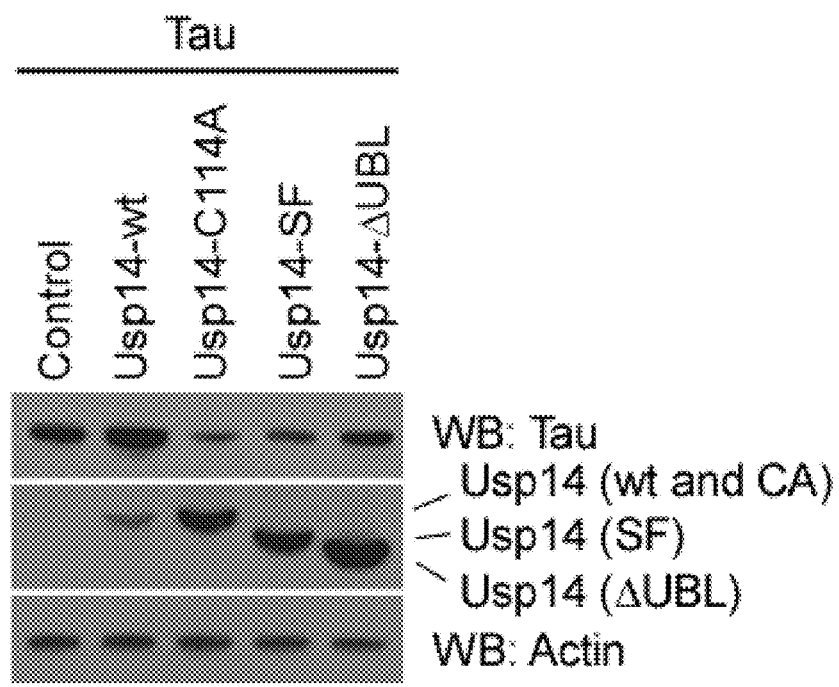

An effect of Usp14 on Tau degradation in human cells was observed in the human cell line, HEK293. Tau was coexpressed with exogenous wild-type or catalytically inactive Usp14 and Tau protein levels were determined by western blot. Expression of wild-type Usp14, but not enzymatically inactive Usp14, stabilized Tau in the human cell line (FIG. 6). In fact, expression of enzymatically inactive Usp14 in HEK293 cells resulted in accelerated Tau degradation (FIG. 6B). This dominant negative effect likely reflects the displacement of endogenous, wild-type Usp14 from the proteasome. This hypothesis was confirmed using a mutant form of Usp14 that lacks the N-terminal UBL domain (Usp14-ΔUBL). The N-terminal UBL domain (FIG. 6A) is the principal proteasome-binding site on Usp14. Deletion of the UBL attenuated the dominant negative effect (FIG. 7), indicating that proteasome binding is required for the mediation of this effect.

Figure 7:
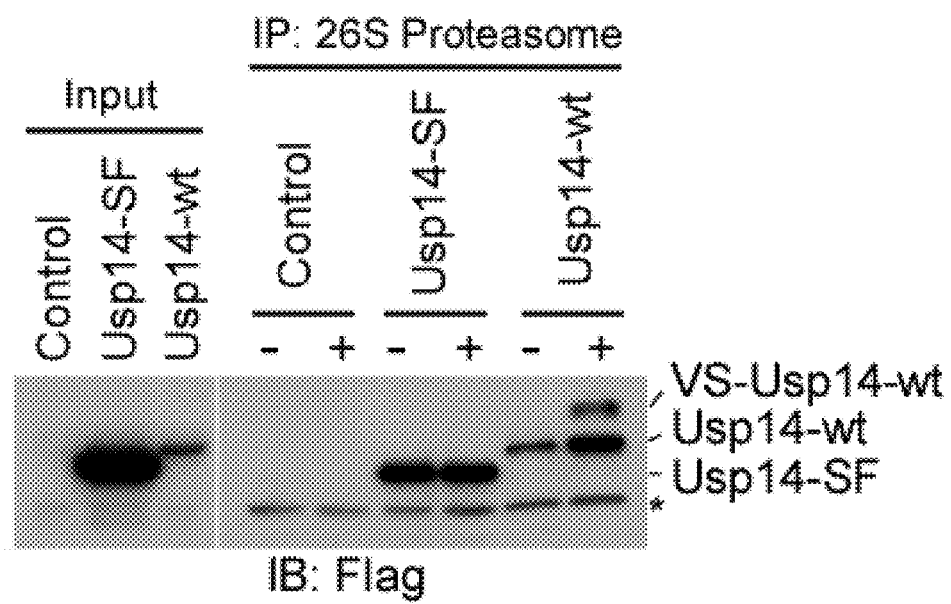
FIG. 7 shows immunoblots that were performed on cellular lysates from 293 cells that co-expressed the indicated forms of flag-tagged Usp14 along with tagged hRpn11 either before (Input) or after (IP:26S Proteasome) proteasome affinity purification and stained using anti-Flag antibody.

The short form (SF) of Usp14 is an endogenous Usp14 splice variant that is expressed from mRNA that lacks a junctional exon (exon 4) between the N-terminal ubiquitin-like domain of Usp14 and its catalytic domain (Wilson et al., (2002), Nat. Genet., 32, 420-425; FIG. 6A). Like the catalytically inactive mutant of Usp14, Usp14-SF exhibited a dominant negative effect on Tau stability in HEK293 cells (FIG. 6A). This suggests that Usp14-SF may be an endogenous inhibitor of Usp14. Consistent with this possibility, Usp14-SF is able to bind proteasome, but unlike the wild-type enzyme, it is not activated enzymatically by proteasome binding (FIG. 7).

Example 4—Specific Inhibitors of Usp14

Figure 8:
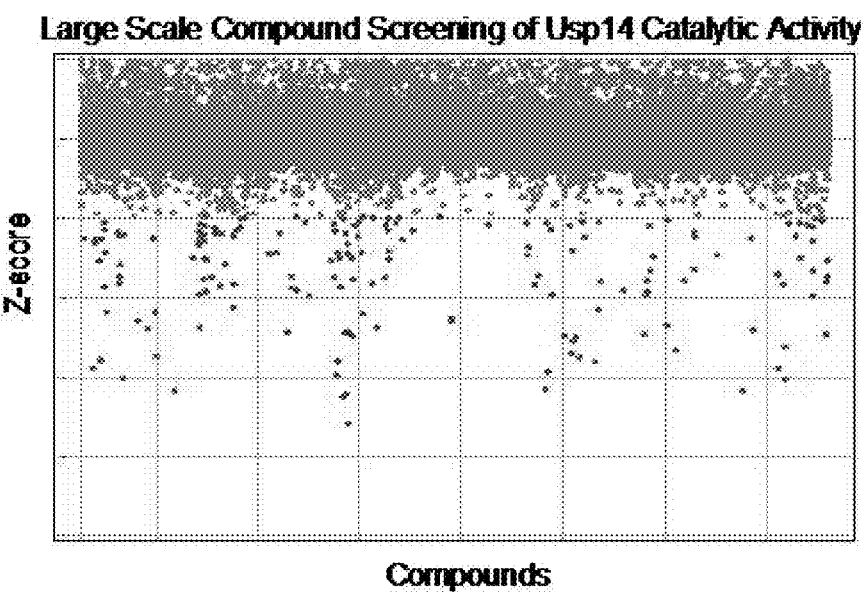
FIG. 8 depicts two panels: panel A shows a statistical plot of the high-throughput large scale compound screening for inhibitors of Usp14 catalytic inhibitors; and panel B shows a frequency distribution curve used to determine AMC quenching compounds.
Figure 8:
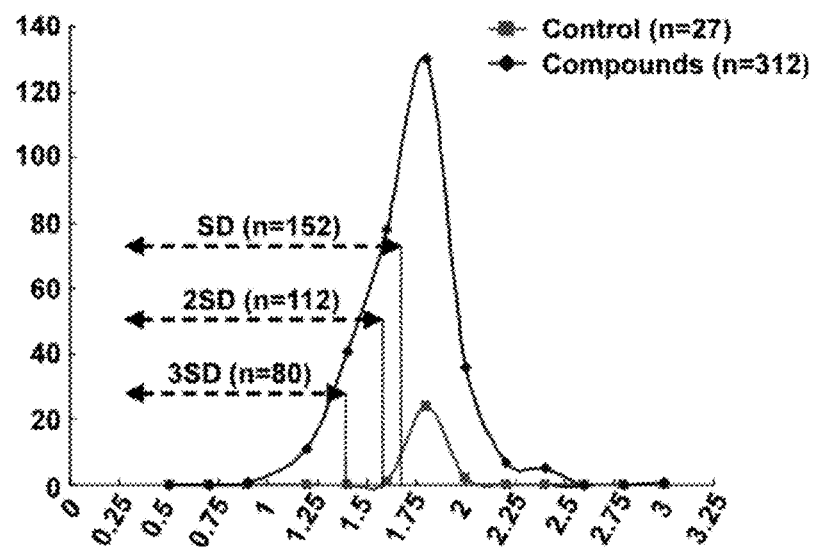

As demonstrated above, chain trimming at the proteasome by Usp14 is a key regulatory step in the ubiquitin-dependent proteolytic pathway. Therefore, in order to identify enhancers of proteasome function, a high-throughput screen for small molecule Usp14 inhibitors was performed using VS-proteasomes reconstituted with recombinant Usp14 and assayed with Ub-AMC (FIG. 8).

Compounds were screened for Usp14/26S inhibition in 384-well low-volume plates in duplicate. Data processing was done by a robust Z-score method and each compound was plotted using Spotfire software. Compounds over the cut-off of Z>5 were mostly autofluorescent and were therefore not counted. To exclude quenching compounds that only affect AMC fluorescence, 312 primary hits were tested for quenching of AMC amine, and pure quenchers were scored as false-positives and excluded from further analysis (FIG. 8B). Of the 63,052 compounds analyzed in the high-throughput screen, 215 were identified as true inhibitors of Usp14.

In order to identify compounds that specifically inhibited Usp14 but were not general deubiquitinase inhibitors, the 215 hit compounds were counterscreened against a panel of deubiquitinating enzymes. Among the hit compounds that inhibited the activity of Usp14 but not any other tested deubiquitinase was IU2-1 (FIGS. 9A-9C).

Example 5—Enhancement of Proteasomal Degradation by IU2-6

Figure 9B:
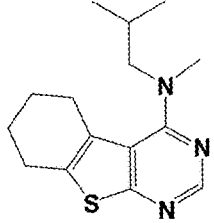
Figure 9B:
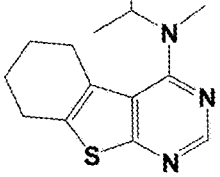
Figure 9B:
Figure 9B:
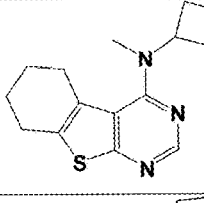
Figure 9B:
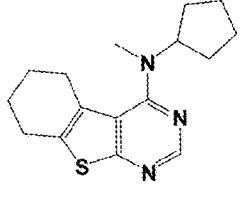
Figure 9C:
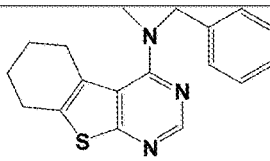
Figure 9C:
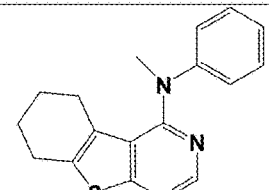
Figure 9C:
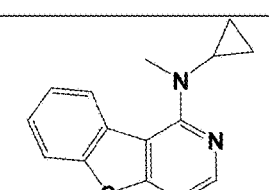
Figure 9C:
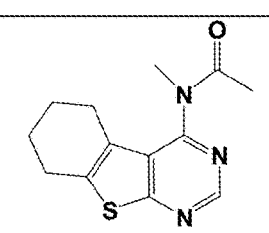
Figure 9C:
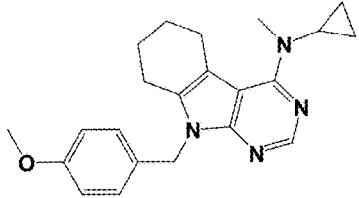
Figure 10:
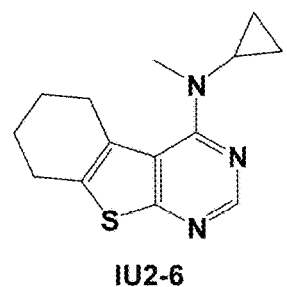
FIG. 10 shows the effectiveness of IU2-6 in promoting Tau degradation. Immunoblots were performed using lysates of MEF cells that co-expressed Tau and Usp14 and that were treated with 0, 25, 50, 75 or 100 μM IU2-6 and stained with antibodies specific for either Tau or Actin.
Figure 10:
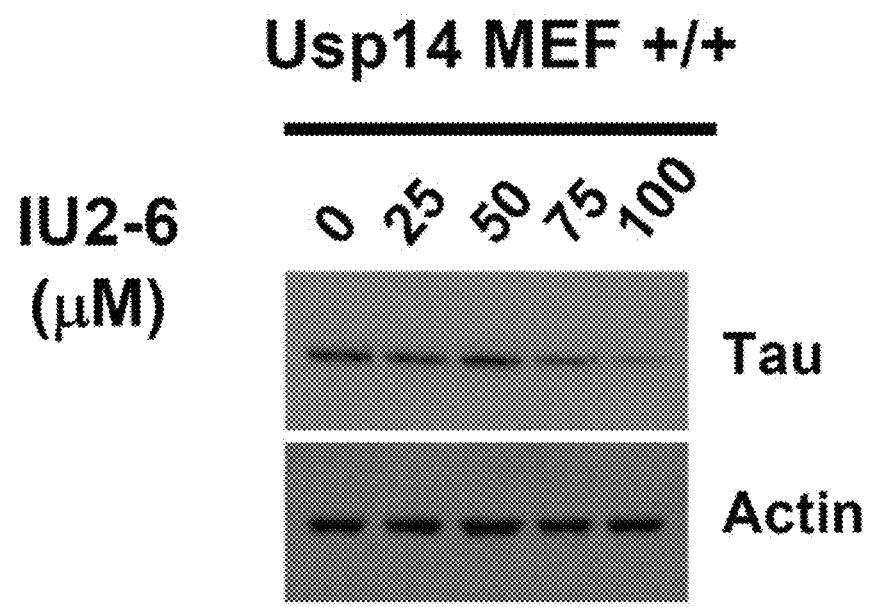

IU2-6 was identified as a specific inhibitor of Usp14 (FIGS. 9A-9C). The ability of IU2-6 to enhance proteasome function in living cells was examined. Tau was used in this experiment because a number of neurodegenerative diseases, including Alzheimer's disease, result from the pathological aggregation of Tau protein. Tau was expressed in MEF cells, which were then treated with IU2-6 at concentrations from 25 to 100 μM. After 36 hours of Tau expression, MEF cells were incubated with 0, 25, 50, 75 or 100 μM of IU2-6 for 6 hours. As seen in FIG. 10, IU2-6 reduced Tau levels at all concentrations tested.

Figure 11:
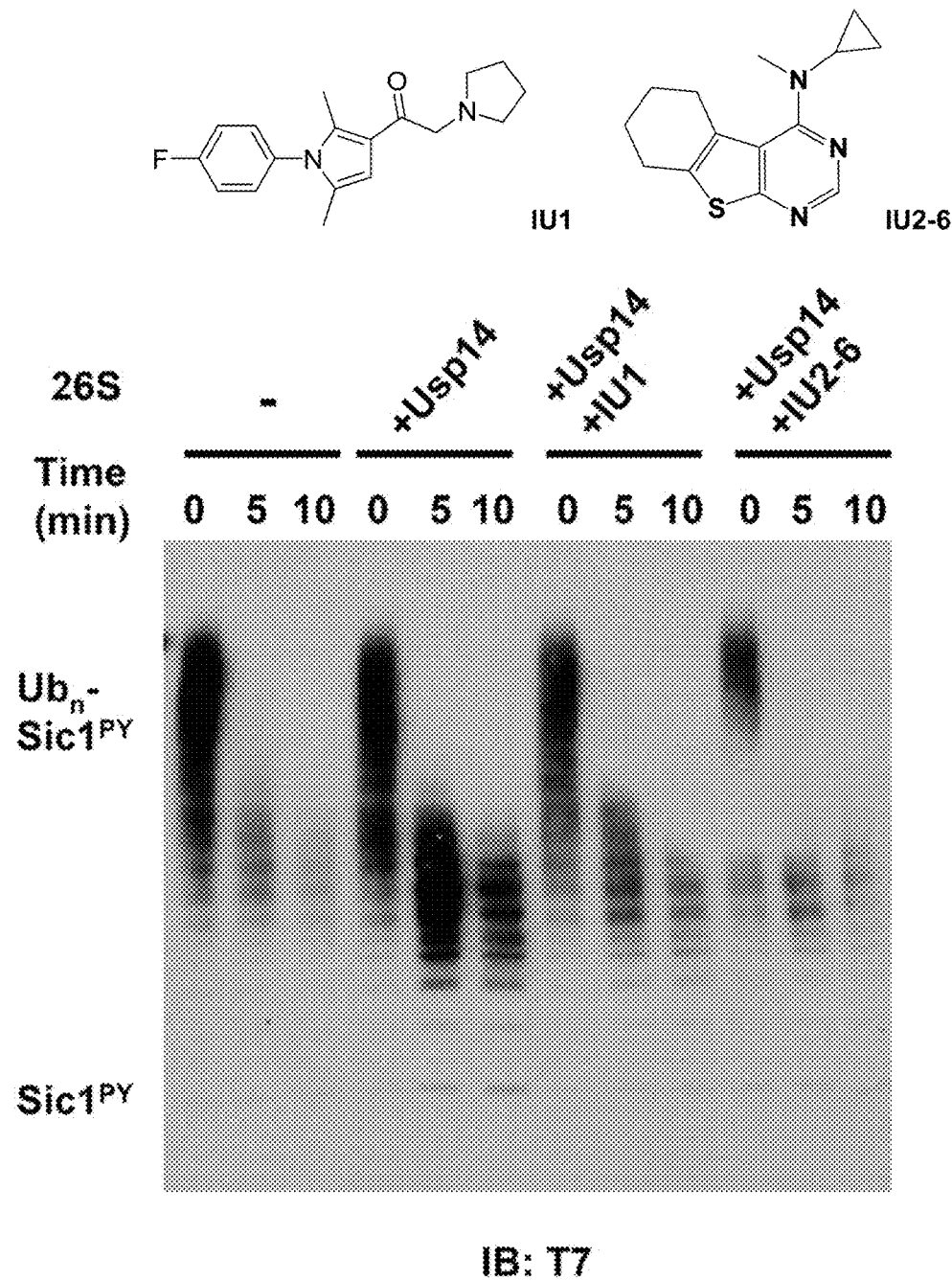
FIG. 11 depicts an immunoblot showing that IU2-6 accelerates proteasome-mediated degradation of $Ub_n$-Sic1$^{PY}$ in vitro. The immunoblot is probed with anti-T7. The T7 epitope tag is on the Sic1$^{PY}$ protein. IU1 is used as a positive control; IU2-6 is comparable in its effect. Lanes marked "−" has proteasome added but no Usp14.
Figure 12:
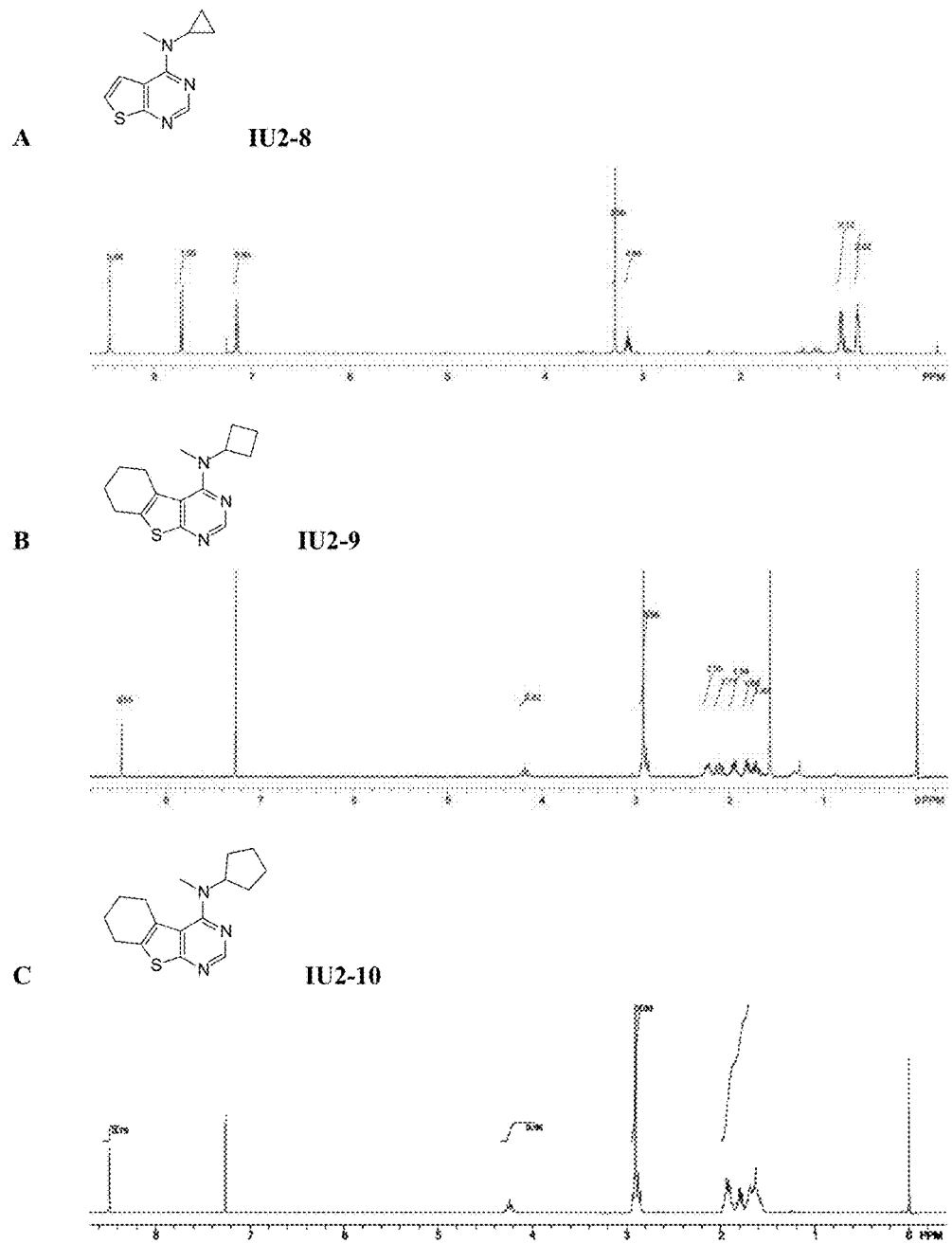
FIG. 12 depicts five panels: panel A depicts the $^1$H NMR spectrum (300 MHz, CDCl$_3$) of IU2-8, panel B depicts the $^1$H NMX spectrum (300 MHz, CDCl$_3$) of IU2-9, panel C depicts the $^1$H NMX spectrum (300 MHz, CDCl$_3$) of IU2-10, panel D depicts the $^1$H NMX spectrum (300 MHz, CDCl$_3$) of IU2-12 and panel E depicts the $^1$H NMX spectrum (300 MHz, CDCl$_3$) of IU2-13.
Figure 12:
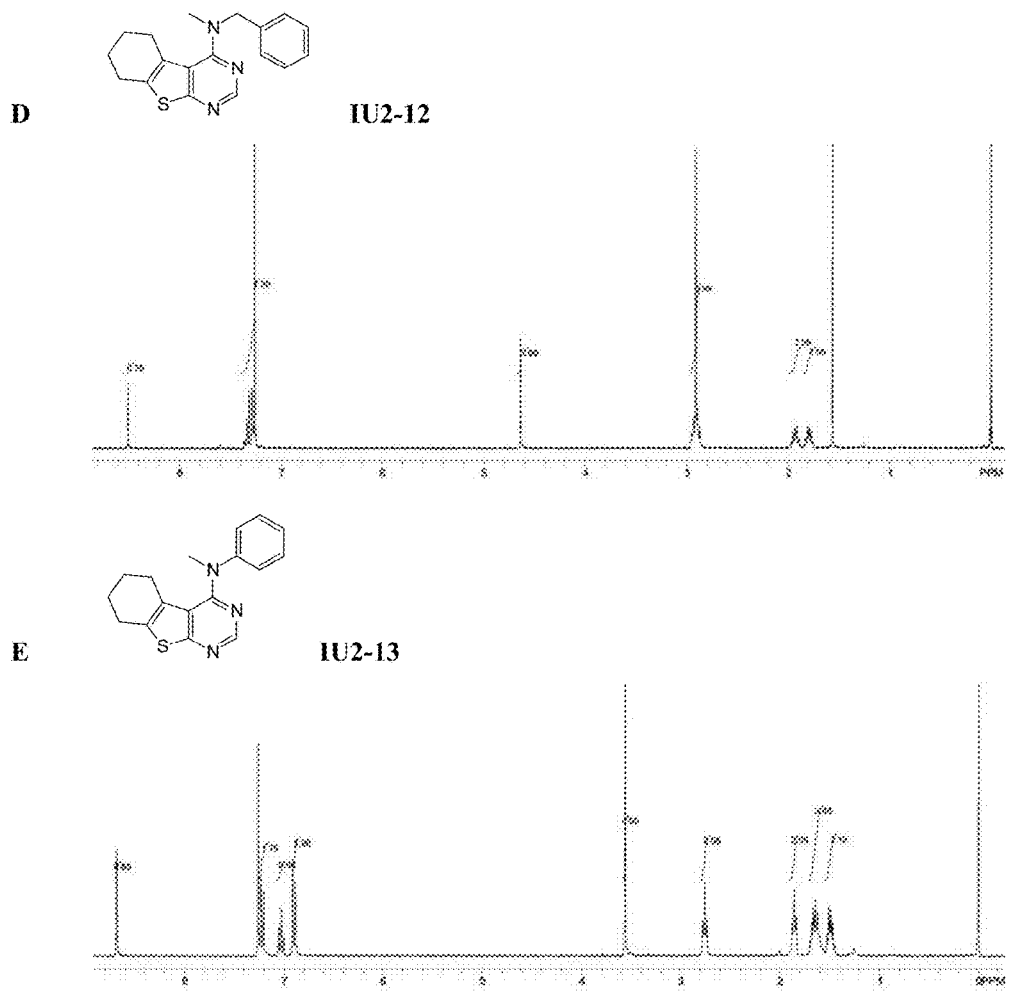

It was next tested whether IU2-6 could serve as an enhancer of ubiquitinated substrate degradation by the proteasome. The effect of IU2-6 on the degradation of ubiquitinated substrates was examined using an in vitro degradation assay using the ubiquitin-dependant proteasome substrate polyubiquitinated $Sic1^{PY}$ ($Ub_n$-$Sic1^{PY}$). $Ub_n$-$Sic1^{PY}$ was incubated with human proteasomes, containing either with or without wild-type Usp14 in the absence or presence of either IU1 or IU2-6. As expected, addition of Usp14 to the proteasome complex enhanced chain trimming and dramatically inhibited substrate degradation. Addition of either IU1 or IU2-6 stimulated the activity of the Usp14-containing proteasomes in degrading $Ub_n$-$Sic1^{PY}$ and inhibited ubiquitin chain trimming (FIG. 11).

EQUIVALENTS

The present invention provides, in part, methods for the enhancement of protein turnover by the proteasome and the treatment of diseases involving either proteasome substrates, upstream components of the ubiquitin-proteasome pathway, or the proteasome itself. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entirety as if each individual publication or patent was specifically and individually indicated to be incorporated by reference. In case of conflict, the present application, including any definitions herein, will control.

We claim:

1. A method of treating a tauopathy in a subject in need thereof comprising administering to the subject an effective amount of a compound represented by formula I:

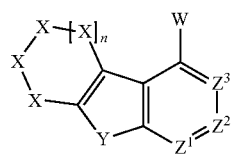

wherein, independently for each occurrence,

W is

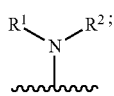

$Z^1$ is

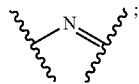

$Z^2$ is

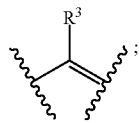

$Z^3$ is

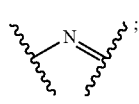 [SMILES: *N=*]

Y is

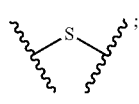 [SMILES: *S*]

X is

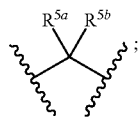

$R^1$ is alkyl, substituted alkyl, heterocyclyl, aryl, aralkyl, heteroaryl, heteroaralkyl, heterocyclylalkyl, cycloalkylalkyl, or alkylcarbonyl;

$R^2$ is alkyl, substituted alkyl, heterocyclyl, aryl, aralkyl, heteroaryl, cycloalkylalkyl, heterocyclylalkyl, heteroaralkyl, or alkylcarbonyl;

$R^3$ is hydrogen, alkyl, halo, haloalkyl, alkoxy, haloalkoxy, amino, or cyano;

$R^{5a}$ is independently hydrogen, halo, lower alkyl or lower haloalkyl;

$R^{5b}$ is independently hydrogen, halo, lower alkyl or lower haloalkyl; and n is 0, 1 or 2; or a pharmaceutically acceptable salt, enantiomer or stereoisomer thereof.

2. The method of claim 1, wherein the tauopathy is selected from the group consisting of frontotemporal dementia, Parkinson's disease, progressive supranuclear palsy, corticobasal degeneration, frontotemporal lobar degeneration and Alzheimer's disease.

3. The method of claim 1, wherein $R^1$ is alkyl, heterocyclyl, aryl, heteroaryl, cycloalkylalkyl, heterocyclylalkyl, aralkyl, heteroaralkyl or alkylcarbonyl.

4. The method of claim 3, wherein $R^1$ is a linear or branched alkyl.

5. The method of claim 1, wherein $R^2$ is methyl, ethyl, cyclopropyl, cyclobutyl, cyclopentyl, phenyl, benzyl, or methylcarbonyl.

6. The method of claim 1, wherein $R^3$ is hydrogen, halo, lower alkyl, lower haloalkyl, cyano, lower alkyloxy, lower haloalkoxy or amino.

7. The method of claim 1, wherein n is 1.

8. The method of claim 1, wherein the compound is selected from the group consisting of

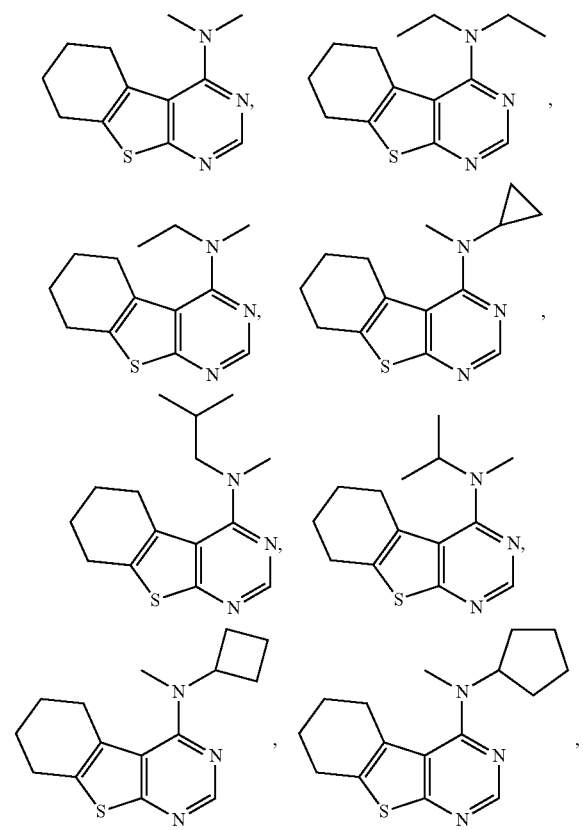

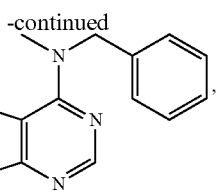

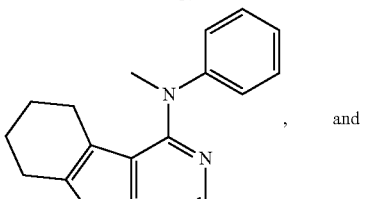

and

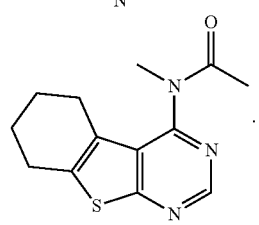

9. The method of claim 1, wherein $R^1$ is a linear or branched alkyl.

10. The method of claim 9, wherein $R^2$ is cycloalkyl or substituted cycloalkyl.

11. The method claim 10, wherein $R^2$ is cyclopropyl or substituted cyclopropyl.

12. The method of claim 7, wherein $R^2$ is cycloalkyl or substituted cycloalkyl.

13. The method of claim 12, wherein $R^1$ is alkyl.

14. The method of claim 13, wherein $R^1$ is a linear or branched alkyl.

15. The method of claim 14, wherein $R^1$ is methyl or ethyl.

16. The method of claim 2, wherein the tauopathy is Parkinson's disease.

* * * * *

UNITED STATES PATENT AND TRADEMARK OFFICE
CERTIFICATE OF CORRECTION

| | |
|---|---|
| PATENT NO. | : 9,981,981 B2 |
| APPLICATION NO. | : 14/572927 |
| DATED | : May 29, 2018 |
| INVENTOR(S) | : Daniel J. Finley et al. |

Page 1 of 1

It is certified that error appears in the above-identified patent and that said Letters Patent is hereby corrected as shown below:

In the Specification

At Column 1, Line 15-18 under the heading GOVERNMENT SUPPORT, please replace:
"This invention was made with U.S. Government support under National Institutes of Health Grant Nos. GM065592, GM66492, and DK082906. The government has certain rights in the invention."

With:
-- This invention was made with government support under GM065592 and GM066492 and DK082906 awarded by National Institutes of Health (NIH). The government has certain rights in this invention. --

Signed and Sealed this
Twenty-fifth Day of October, 2022

*Katherine Kelly Vidal*

Katherine Kelly Vidal
*Director of the United States Patent and Trademark Office*